(12) United States Patent
Saruhan-Brings et al.

(10) Patent No.: US 8,524,181 B2
(45) Date of Patent: Sep. 3, 2013

(54) SENSOR-INTEGRATED DEVICE

(75) Inventors: Bilge Saruhan-Brings, Niederkassel (DE); Mathias Christian Stranzenbach, Berlin (DE); Christoph Leyens, Dresden (DE)

(73) Assignee: Deutsches Zentrum Fuer Luft-und Raumfahrt e.V. (DE)

( * ) Notice: Subject to any disclaimer, the term of this patent is extended or adjusted under 35 U.S.C. 154(b) by 445 days.

(21) Appl. No.: 12/993,342

(22) PCT Filed: Jul. 14, 2009

(86) PCT No.: PCT/EP2009/058954
§ 371 (c)(1),
(2), (4) Date: Jan. 25, 2011

(87) PCT Pub. No.: WO2010/015490
PCT Pub. Date: Feb. 11, 2010

(65) Prior Publication Data
US 2011/0126515 A1 Jun. 2, 2011

(30) Foreign Application Priority Data
Aug. 5, 2008 (DE) .......... 10 2008 036 370

(51) Int. Cl.
*B01D 53/56* (2006.01)
*B01D 53/86* (2006.01)
*B01D 53/94* (2006.01)
*B01J 23/40* (2006.01)
*B05D 1/00* (2006.01)
*B05D 5/00* (2006.01)
*C23C 16/00* (2006.01)
*F01N 3/10* (2006.01)
*F01N 3/28* (2006.01)
*G01N 35/00* (2006.01)

(52) U.S. Cl.
USPC .............. 423/213.2; 423/213.5; 423/213.7; 423/239.1; 502/325; 502/439; 502/514; 502/527.12; 502/527.24; 60/274; 60/276; 60/299; 60/301; 73/23.2; 73/23.31; 73/31.03; 427/58; 427/446; 427/596

(58) Field of Classification Search
USPC ..... 423/213.2, 213.5, 213.7, 239.1; 502/325, 502/439, 514, 527.12, 527.24; 60/274, 276, 60/299, 301; 73/23.2, 23.31, 31.03; 427/58, 427/446, 596
See application file for complete search history.

(56) References Cited

U.S. PATENT DOCUMENTS

| | | | |
|---|---|---|---|
| 4,869,094 A * | 9/1989 | Kozuka et al. ................ | 73/23.2 |
| 5,431,012 A | 7/1995 | Narula et al. | |
| 8,048,384 B1 * | 11/2011 | Bokerman et al. ............ | 422/400 |
| 2009/0159445 A1 * | 6/2009 | Krishna et al. ................ | 204/424 |

FOREIGN PATENT DOCUMENTS

| DE | 4334672 A1 | 4/1995 |
|---|---|---|
| EP | 0331050 B1 | 9/1989 |

(Continued)

OTHER PUBLICATIONS

B. Saruhan, M. Stranzenback, G.S. Mondragon Rodriguez, "An integrated solution for NOx-reduction and-control under lean-burn conditions", Mat.-wiss. u. Werkstofftech. 2007, 38, No. 9. pp. 725-733.

*Primary Examiner* — Timothy Vanoy
(74) *Attorney, Agent, or Firm* — Clements Bernard PLLC; Gregory N. Clements

(57) ABSTRACT

The invention relates to a device for the qualitative and/or quantitative determination of at least one component of a chemically reducible gas mixture, an exhaust gas catalytic converter utilizing such a device, a vehicle including such a catalytic converter, a process for preparing such a device, a process for monitoring the $NO_x$ emissions of a vehicle, and the use of such a device.

19 Claims, 1 Drawing Sheet

(56) References Cited

FOREIGN PATENT DOCUMENTS

Figure 1:
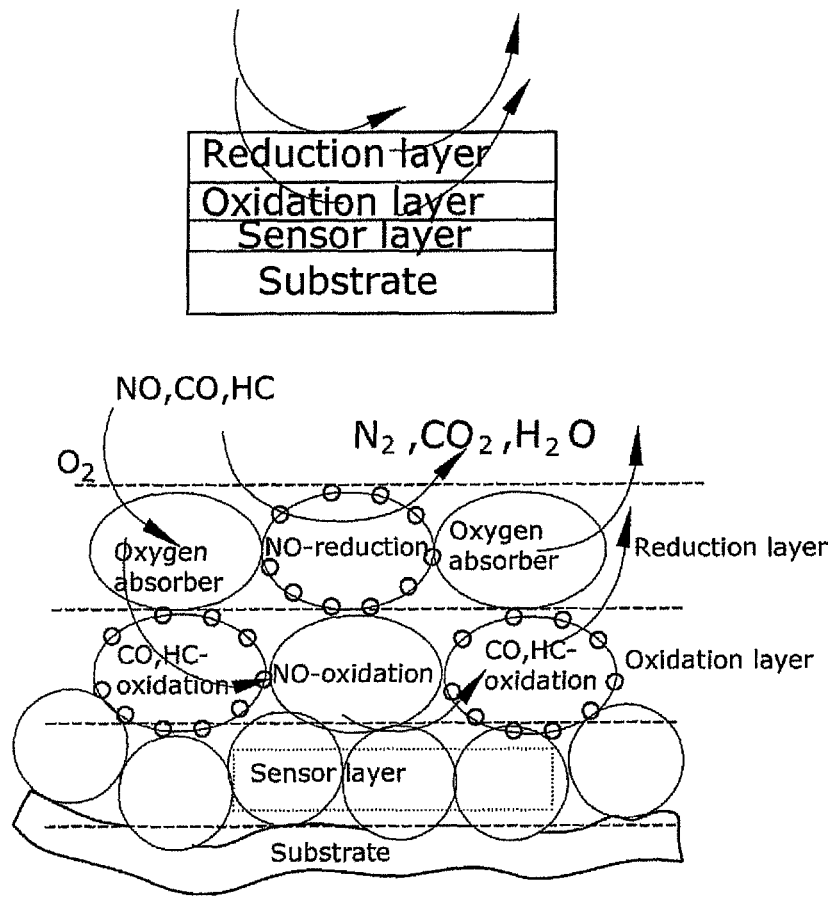

| | | |
|---|---|---|
| EP | 0769096 B1 | 4/1997 |
| EP | 1389268 B1 | 2/2004 |
| JP | 61212075 | 3/1988 |
| JP | 61268911 | 5/1988 |
| JP | 5-196569 A * | 8/1993 |

\* cited by examiner

SENSOR-INTEGRATED DEVICE

The invention relates to a device for the qualitative and/or quantitative determination of at least one component of a chemically reducible gas mixture, an exhaust gas catalytic converter utilizing such a device, a vehicle including such a catalytic converter, a process for preparing such a device, a process for monitoring the $NO_x$ emissions of a vehicle, and the use of such a device.

An exhaust gas catalytic converter, also briefly referred to as "converter" (colloquially, "cat" or "catcon"), serves for exhaust gas aftertreatment in vehicles having an internal combustion engine. The pollutant emissions from exhaust gas can be reduced drastically by a converter. In general, the whole system for exhaust gas aftertreatment, not just the catalyst part, is referred to as an "exhaust gas catalytic converter".

The catalytic converter usually consists of several components. A thermally stable honeycomb structure made of ceramics (monolith) or metal foils (Metalit) and comprising a large number of thin-walled passages serves as a support. The support is covered by the so-called washcoat. It consists of highly porous alumina ($Al_2O_3$) and oxygen storage components, such as cerium oxide, and serves to increase the surface area. By the high surface roughness, a very large surface area is realized (up to several thousand square meters). The catalytically active precious metals are incorporated in the washcoat. In modern catalytic converters, the precious metals are platinum, rhodium and/or palladium. The ceramic support is supported in a metallic housing by means of specific mats (usually fiber mats, less frequently knitted wire meshes) in a step referred to as "canning". The canning of the metal catalysts is narrowed down to welding the metal catalyst into the exhaust gas system. Special mats or a separate metal housing are not necessary. The housing is permanently mounted in the exhaust gas system of the vehicle and in part has further possibilities of connection, for example, for oxygen sensors or thermocouples. There are also metal catalysts with integrated oxygen sensors.

The mode of action of catalytic converters is based on catalytic reactions. The function of a catalytic converter is the chemical conversion of the combustion pollutants hydrocarbons ($H_mC_n$), carbon monoxide (CO) and nitrogen oxides ($NO_x$) to the non-toxic substances carbon dioxide ($CO_2$), water ($H_2O$) and nitrogen ($N_2$) by oxidation or reduction, respectively. Depending on the operating point of the engine, conversion rates near 100% can be reached under optimum operation conditions.

In particular, the following three different catalyst types are of importance to the present invention:
1. Three-Way Catalytic Converter:

In a three-way catalytic converter (TWC), the oxidation of CO and $H_mC_n$ and the reduction of $NO_x$ take place in parallel: $H_mC_n$ is oxidized by $O_2$ to $CO_2$ and $H_2O$, CO is oxidized by $O_2$ to $CO_2$, and $NO_x$ is reduced by CO to $N_2$ and $CO_2$.

A precondition thereof is a constant air-fuel mixture in a stoichiometric ratio ($\lambda=1$) of 14.7 g of air per g of gasoline fuel. A slight deviation into the lean range ($\lambda>1$) already causes a sudden rise of nitrogen oxide emission downstream of the catalyst, since there is too little CO for the reduction. Therefore, the mixture is controlled between a stoichiometric and slightly rich ratio. The three-way catalytic converter can be employed only in vehicles with a gasoline engine and closed-loop A/F control. In a diesel engine, the excess oxygen in the exhaust gas prevents the reduction of the $NO_x$ and necessitates specific catalysts.

2. $NO_x$ Storage Catalytic Converter:

Modern lean-burn engines operate in an oxygen excess to increase the efficiency of the engine. Therefore, conventional catalysts cannot be employed. The oxidation of CO and $H_mC_n$ is still possible in an oxygen excess ($\lambda>1$) by analogy with a conventional three-way catalytic converter, but nitrogen oxides ($NO_x$) have to be stored temporarily. Their catalytic reduction is achieved only in a stoichiometric to rich exhaust gas mixture. Therefore, these novel engines require a further developed type of converters with additional chemical members that allow for the storage of nitrogen oxides.

If the storage capacity of the catalyst is exhausted, a rich, reducing exhaust gas mixture is briefly (for about two seconds) adjusted by the engine electronics. In this brief rich phase, the nitrogen oxides stored temporarily in the catalyst are reduced to nitrogen, and thus the catalyst is prepared for the next storage phase. By this procedure, it is also possible to minimize the pollutant emissions of economic lean-burn engines and to meet valid limits of the European standards. The storage capacity (about 60 to 90 seconds) is monitored by an $NO_x$ sensor.

In order to achieve this temporary storage of the nitrogen oxides, a precious metal catalyst, such as platinum, and an $NO_x$ storage component, which is mostly an alkaline earth metal, such as barium, are applied to suitable supports. In the lean, i.e., oxygen-rich, atmosphere, the nitrogen oxides are oxidized under the catalytic effect of the precious metal catalyst, absorbed to form nitrates, such as barium nitrate, in the catalyst and thus removed from the exhaust gas stream. During the regular short "fuel-enriching", these reactions proceed in the opposite direction, whereby the $NO_x$ are again released into the exhaust gas stream and further reduced by the reducing components present in the rich atmosphere, such as $H_mC_n$ (incompletely combusted hydrocarbons) or CO. The storage converter can store $NO_x$ only in a temperature range of from 250 to 500 degrees centigrade. This temperature window is achieved by triple-flow exhaust gas pipes or exhaust bypasses.

3. SCR (Selective Catalytic Reduction)

Another targeted and by now marketable process for reducing nitrogen oxides is selective catalytic reduction. In this approach, an aqueous urea solution (commercial name AdBlue) is continuously injected into the exhaust gas stream, from which water and ammonia are formed by hydrolysis. The thus formed ammonia can reduce the nitrogen oxides in the exhaust gas to nitrogen.

Today, the monitoring of the composition of the exhaust gas stream of a catalytic converter is effected by means of an oxygen sensor on a standard basis.

The measurement is based on the residual oxygen content in the exhaust gas. It is the main sensor in the control loop of closed-loop A/F control for catalytic exhaust gas purification (colloquially, closed-loop converter). Two measuring principles are used: the voltage of a solid electrolyte (Nernst sensor) and the change in resistance of the ceramics (resistance sensor).

Of these two types of sensors, the Nernst sensor is by far more common, and therefore, it will be briefly described in the following.

In the Nernst sensor, one side of the ceramic sensor element is exposed to the exhaust gas stream while the other side contacts an oxygen reference. It usually uses the ambient air for this purpose, either through an aperture directly at the sensor or via the supply line and the plug. This hinders the so-called reference air poisoning by water, oil or fuel vapors. This would reduce the oxygen content of the reference and the sensor voltage. With a pumped reference, the ambient air is no longer required, but the oxygen reference is produced by an imposed oxygen ion stream from the exhaust gas.

At temperatures of above about 300° C., the yttrium-doped zirconium dioxide ceramic material of the sensor becomes conductive for negative oxygen ions. The difference is concentration produces an ion diffusion towards the exhaust gas. The oxygen atoms can permeate the ceramics as doubly negative charged ions. The electrons required for the ionization of the oxygen atoms are supplied by the electronically conductive electrodes. Thus, a voltage can be sensed between the platinum electrodes provided on the inside and on the outside, the so-called probe voltage. It is transmitted through the wires to the engine control device. It is from 0 to 150 mV for $\lambda>1$ (lean mixture, excess air), and from 800 to 1000 mV for $\lambda<1$ (rich mixture, excess fuel). The voltage is described by the Nernst equation. In a very narrow transition zone around $\lambda=1$, the so-called $\lambda$ window, the characteristic is extremely steep. In this zone, the voltage changes almost abruptly as a function of the air-to-fuel ratio.

In gasoline engines, the sensor is usually mounted into the exhaust manifold or briefly downstream of the collector. In vehicles with high legal demands on exhaust gas purification and self-diagnosis, several sensors are employed, usually for each cylinder bank in V-engines, up to one sensor per cylinder for a selective cylinder closed-loop control.

The correct lambda ratio is an important parameter for controlling the combustion and for enabling the exhaust gas purification by the three-way catalyst. In the automotive field, the oxygen sensor became established first in the U.S. and then in Europe as well due to the legal restrictions.

The first oxygen sensors were constructed as "finger probes", the actual sensor element being formed like a thimble, with the exhaust gas outside and the reference air inside.

Increasingly, the sensors are constructed in planar technology from several layers, wherein the probe heating is already integrated.

The ceramic element is surrounded by a so-called protective tube. It facilitates the keeping of the sensor element at the desired temperature and prevents mechanical damage. For the access of gas, the protective tube is provided with holes.

The oxygen sensor permanently compares the residual oxygen content in the exhaust gas with the atmospheric oxygen content and transmits this value as an analog electric signal to a control device, which uses it together with other characteristics to produce a control signal for forming the mixture, which generally causes the injected amount to be adjusted in a gasoline engine. In OBD vehicles, the function of the closed-loop control oxygen sensor and the monitoring sensor must be supervised by the control device. The supervision is effected sporadically.

A significant disadvantage in the use of oxygen sensors generally resides in the relatively high costs incurred by such sensors. In addition, they must be integrated into the converter or at positions upstream and/or downstream from the converter, which is complicated. Also, a direct function control of the converter is not possible using such oxygen sensors.

A first way out of this lack of direct monitoring seems to be found in temperature sensors as described, for example, in U.S. Pat. No. 5,431,012, EP 1 389 268 B1 and EP 0 769 096 B1. However, it is not possible to monitor the exhaust gas composition by means of such temperature sensor integrated exhaust gas converters. In this respect, gas sensor integrated exhaust gas converters would be desirable; however, such have not been described to date.

The combination of a catalyst with a gas sensor is described, for example, in "An integrated solution for $NO_x$-reduction and -control under lean-burn conditions" (B. Saruhan, M. Stranzenbach, G. C. Mondragón-Rodríguez, Mat.-wiss. U. Werkstofftech. 2007, 38, 725 to 733). However, such a combination is not suitable for use in a catalytic converter, since the catalyst and the gas sensor are separated in space.

Thus, it is an object of the present invention to provide a gas sensor integrated device that can be inserted, for example, in an exhaust gas catalytic converter, that allows for a direct functional monitoring of the catalyst and, in addition, can be realized at low cost.

In addition, it is a further object of the present invention to be able to effect the integration of the gas sensor in such a way that it can be used for determining the ageing condition of the catalyst.

In a first embodiment, the object of the present invention is achieved by a device for the qualitative and/or quantitative determination of at least one component of a chemically reducible gas mixture, comprising:

a) a reduction layer for the chemical reduction of at least one component of the gas mixture;

b) an oxidation layer for the partial or complete back oxidation of the component(s) chemically reduced by the reduction layer; and c) a selective gas sensor electrode for the qualitative and/or quantitative determination of at least one of the back-oxidized components.

The reduction layer, the oxidation layer and the selective gas sensor electrode are at first to be considered as entities independent in space, which means, in particular, that these layers or electrodes are not necessarily in contact with each other. However, the independence in space of these at least three components of the device can be realized only to the extent as to be integrated in one construction element, which clearly delimits the design of this device according to the invention from that in the publication "An integrated solution for $NO_x$-reduction and -control under lean-burn conditions" as mentioned above (the latter further also lacking an oxidation layer).

In this context, the terms "(chemical) reduction" and "oxidation" do not necessarily mean the loss or uptake of oxygen. Rather, the terms "reduction" and "oxidation" in the present case are intended to refer to the decreasing or increasing, respectively, of the oxidation states of the elements in question. Also, the term "back oxidation" is not to be understood in a limiting way, i.e., a starting compound A once reduced to a compound C need not necessarily be oxidized back to A. Rather, reduction to a compound B having a medium oxidation state between the oxidation states of compounds A and C is also possible.

Preferably, the gas sensor electrode or/and the reduction layer or/and the oxidation layer are bonded to a support substrate. This support substrate provides the device according to the invention with additional stability and enables almost any mutual arrangement of said at least three components of the device.

Preferably, the support substrate is a ceramic honeycomb structure or a metal foil. In the cases where the support substrate is electrically conductive, as with a metal foil, for example, it is to be taken care that the support substrate is electrically insulated from the metallic catalyst particles that may be present in the reduction and/or oxidation layer. This may be achieved, for example, by additionally applying a catalytically inert layer (for example, $Al_2O_3$).

Preferably, the at least three components of the device, i.e., the reduction layer, the oxidation layer and the selective gas sensor electrode, are arranged in such a way that the component to be reduced/oxidized passes first the reduction layer and then the oxidation layer on its way from the gas mixture to the gas sensor electrode. By such a structure, a precise and reproducible detection of the back-oxidized component by the gas sensor electrode selective for it can be achieved.

This situation can be illustrated by a schematic representation of the detection of $NO_2$ in an exhaust gas stream (cf. FIG. 1): After the combustion, the resulting exhaust gas stream contains the further undesirable combustion products, such as $NO_x$, CO and UHC (unreacted hydrocarbons) in addition to the primary combustion products $CO_2$ and $H_2O$. As initially described, it is the function of any kind of exhaust gas catalytic converter to convert these three components to $N_2$, $CO_2$ and $H_2O$. Now, when these three components hit the reduction layer at first, they are reacted completely to $N_2$, $CO_2$ and $H_2O$ under sufficiently reducing conditions. However, in the case of too lean reaction conditions, part of these components remains unreacted, and in particular, not all $NO_x$ is completely reduced to $N_2$. When these unreacted $NO_x$ hit the oxidation layer, they are oxidized to $NO_2$ and subsequently detected by the $NO_2$-selective gas sensor electrode. Thus, the $NO_2$-selective gas sensor electrode detects an $NO_2$ concentration other than 0 only if the fuel-to-air ratio is not optimally adjusted.

Now, it is readily understood that such a selective detection is substantially more difficult to achieve when the reduction and oxidation layers are independently arranged.

Further, it is preferred that the gas sensor electrode has a thickness within a range of from 1 to 5 µm.

Lower layer thicknesses are in disadvantage in that a satisfactory function of the gas sensor electrode is no longer ensured. Larger layer thicknesses are in disadvantage because they involve a higher process expenditure in the preparation and, above all, higher cost.

Preferably, the gas sensor electrode is a simple or binary or doped transition metal oxide (e.g., $TiO_2$), or a semiconductor oxide (e.g., $SnO_2$). The doping elements are Fe, Zn, Zn/Al, Cu, Pt, Al, Nb for $TiO_2$ and Cu, Al, Au and W for $SnO_2$, with 1-6 atomic percent each.

The reduction and oxidation layers are preferably gas-permeable layers of at least one complex oxide having a spinel, perovskite or aluminate structure and additionally comprise at least one precious metal. The precious metal of the reduction layer is preferably Pd, Rh, and the precious metal of the oxidation layer is preferably Pt.

The precious metals incorporated in the lattice of a complex oxide will reduce pollutant gases much more effectively, require an at least three times lower proportion of precious metal and are more stable towards thermal ageing (coarsening or sintering of precious metal is avoided by incorporating and eliminating the precious metal in and out of the lattice of the complex oxide).

In addition, in the case of a metallic support substrate, an electrically insulating layer is to be used thereon.

The support materials preferably include highly porous, especially ceramic, structures based on silicon oxide, cerium oxide and/or aluminum oxide, for example, those available by sol-gel processes well-known in the prior art including cordierite, mullite and/or aluminum titanate.

The reduction layer preferably has a thickness within a range of from 10 to 20 µm, and the oxidation layer preferably has a thickness within a range of from 1 to 10 µm.

The reduction layer must have a minimum layer thickness in order that the undesirable components contained in the exhaust gas can be reduced in satisfactory quantity. Greater layer thicknesses are associated with correspondingly higher costs again, the precious metal(s) contained in the support metal contributing a great deal, in particular.

Analogous arguments relating to preferred layer thicknesses are also valid for the oxidation layer (i.e., insufficient oxidation of $NO_x$ to $NO_2$ when the layer thickness is too low; too high cost when it is too great).

Further, it is preferred that at least two gas sensor electrodes are arranged spatially one behind the other with respect to a flow direction of the gas mixture. This design has the advantage that the detection can be effected throughout the length of the converter. Thus, when the converter is segmented in this way, information about the ageing condition of the catalyst can be obtained, since the catalytic activity moves downstream with the ageing in the catalyst, and therefore, the sensors may indicate different $NO_x$ values in the flow direction of the gas mixture. In addition, the temperature dependence of the resistor sensors caused by the driving dynamics can also be remedied by this kind of arrangement. The variations can then be compensated by comparative measurements between two sensor elements. Thus, the sensor signal is generated from the resistance difference or quotient between the individual signals.

In a second embodiment, the object of the invention is achieved by an exhaust gas catalytic converter, especially a three-way catalytic converter, a selective catalytic reduction (SCR) converter, or an $NO_x$ storage catalytic converter, comprising a device according to the invention as described above.

Such converter/sensor layers can be employed in all combustion applications: Further examples would include: low-pressure turbine of an airplane, a stationary turbine, combustion and heating systems, hydrogen generator and purifier systems, etc.

In a third embodiment, the object of the invention is achieved by a vehicle containing a built-in exhaust gas catalytic converter according to the invention.

In a fourth embodiment, the object of the invention is achieved by a process for preparing a device according to the invention, characterized in that a gas sensor electrode, optionally supported on a support substrate, is provided and coated with oxidation and reduction layers. In the case of a metallic support substrate, an electrically non-conductive layer (e.g., $Al_2O_3$) is provided between the substrate and the electrode.

The gas sensor electrode is preferably produced by CVD, PVD, sol-gel, plasma spraying, screen printing, PLD, plating or immersion processes.

The oxidation and/or reduction layer, especially the support material of those layers, is preferably prepared by a sol/gel process. This may be realized, for example, by adding a precursor of the precious metal catalyst to a sol precursor of the support material, and impregnating the support substrate with such a sol and/or a gel correspondingly prepared therefrom. After drying, the washcoat is obtained, in which the precious metal catalyst particles are formed from their precursors by reduction after a short start-up period.

Perovskites (or spinels or aluminates) with integrated precious metals prepared by a sol-gel process can also be applied to the support substrate via powdery precursors in a dipping method after admixing a binding oxide (e.g., silicon oxide).

In a fifth embodiment, the object of the invention is achieved by a process for monitoring the $NO_x$ emissions of a vehicle, characterized in that the air-to-fuel ratio is varied as a function of the amount(s) of the component(s) for which the gas sensor electrode is selective.

In a sixth embodiment, the object of the invention is achieved by the use of a device according to the invention for the qualitative and/or quantitative determination of at least one component of a chemically reducible gas mixture.

In particular, said component is an $NO_x$ compound, especially $NO_2$. Other emission and gas types (e.g., $CO_2$, $H_2$, UHC—unburned hydrocarbons) are also included by using corresponding sensor/catalyst layers.

It is further preferred that the gas mixture is the exhaust gas of an internal combustion engine.

FIG. 1 shows an example of a device according to the invention and its use within an exhaust gas catalytic converter (each in sections).

Figure 2:
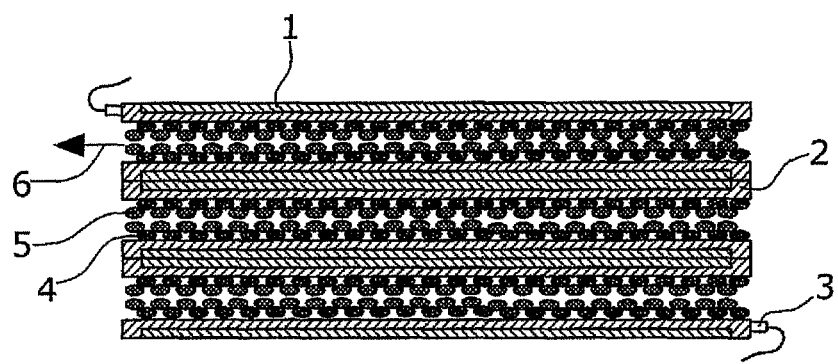

FIG. 2 shows in more detail the actual structure of the exhaust gas catalytic converter: At first, one or more gas sensor electrodes (2) connected with a detecting unit (not shown) through the lead(s) (3) are applied to a support substrate (1). In the direction of the interior space of the support substrate (1), the gas sensor electrode (2) is followed by the oxidation layers(s) (4) and the reduction layer(s) (5). Such a structure ensures that the components of the exhaust gas stream (6) must pass first the reduction layer(s) (5) and subsequently the oxidation layer(s) (4), before the components, which may be chemically modified, can hit the gas sensor electrode (2).

To conclude, the invention described realizes a general, i.e., higher-level, inventive concept, namely that the whole system performs at least two functions, and at least one material of this system with its properties participates in at least two functions. In addition, these functions of the material system can interact with one another by internal or external control under the influence of external stimulations (of a mechanical, chemical or physical nature).

EXAMPLES

Example I

An $Al_2O_3$ plate having a thickness of 0.5 mm was subjected to reactive coating for the first time with 4 atomic percent of Cu-doped $TiO_2$ from two sources by magnetron sputtering methods. Typically, a coating time of 1-2 hours yields a layer thickness of 3-5 µm. The coated plate was subsequently annealed at 900° C. for crystallization and for incorporating a porous morphology.

Sols based on the citrate and coprecipitation method were used to prepare the catalyst reduction and catalyst oxidation layers.

The catalyst oxidation layer with $BaTi_{(1-z)}Pt_zO_3$ was achieved by coprecipitation of Ba and Pt nitrate solutions by adding Ti solution. The barium-based solution was prepared by dissolving metallic barium pieces in ethanol with continuous stirring over night. Dehydrated Pt nitrate was added to the Ba solution. The Ti solution was prepared by dissolving titanium isopropoxide (99.99%) in 2-propanol. The coprecipitation was achieved by rapid admixing of the Ti solution into the Ba/Pt solution. After a homogeneous sol had been obtained, the solvents were removed on a rotary evaporator at 80° C. The gel obtained was calcined at temperatures of up to 900° C., followed by grinding for 60 minutes.

The catalyst reduction layer with the composition $LaFe_xCo_{(1-x-y)}Pd_yO_3$ was prepared from a citrate sol formed from three aqueous solutions (La acetate, Co acetylacetonate and Fe nitrate). In addition, an aqueous Pd nitrate solution in 30% by volume $HNO_3$+ water was prepared in a desired proportion (y) and admixed with the Fe nitrate solution. The Pd/Fe nitrate solution was introduced into the Co solution with the addition of a stoichiometric amount of citric acid. The citric acid forms complexes with metal cations. The resulting solution was mixed with the La solution with continuous stirring and addition of ethylene glycol (at a 40:60 mass ratio to citric acid). The solvent of the sol was removed on a rotary evaporator at 80° C. This resulted in the formation of a foamy solid, which was slightly comminuted by a mortar and pestle, calcined at temperatures of 500-900° C. for 3 hours, and then ground for 60 minutes.

The fine-grained powder obtained was added to the citrate or coprecipitation sol at a solid-to-liquid ratio of 10:90. The plate precoated with doped $TiO_2$ was first coated with the catalyst oxidation layer and then with the catalyst reduction layer. Thus, the plate coated with the sensor layer was immersed into the sol+powder mixture, allowed to dwell therein for a few minutes, and then withdrawn. The drying process was performed in three steps: at first, the coated plates were dried in the air for 1-2 hours and subsequently in a drying oven at 80° C. for at least 3 hours. This procedure was repeated three times. Coatings thus obtained were subsequently annealed at 900° C. for 3 hours.

Example II

For the preparation of Cu-doped Ti sol, titanium isopropoxide was dissolved in 2-propanol and hydrolyzed with an aqueous Cu nitrate solution. A cordierite (Al—Mg spinel) honeycomb structure was immersed into this colloidal sol and withdrawn. The excess sol was removed by compressed air. The coated honeycomb structure was dried in the air at first and then in a drying oven at 150° C., followed by annealing at 900° C.

With the $BaTi_{(1-z)}Pt_zO_3$ (see above for catalyst oxidation material) or $LaFe_xCo_{(1-x-y)}Pd_yO_3$ (see above for catalyst reduction material) powders prepared by a sol-gel process and ground, an aqueous suspension was prepared at a 40:60 ratio of solids-to-water. The $TiO_2$-coated plate was immersed into this suspension, withdrawn, and the excess solution was removed by compressed air. This step was repeated three times. After a slow drying process at 150° C., the coatings were calcined at 500-700° C.

The composition of the catalyst oxidation layers may be replaced, for example, by Pt-doped hexaluminates ($LaMnAl_{11}O_{19}$) or $LaSrMnPtO_3$ perovskites.

In the catalyst reduction materials, Rh may also be used instead of Pd.

Ageing and Damage Supervision of the Catalyst

Through a resistance gas sensor integrated in the system, a malfunction of the catalyst caused by ageing and damage is to be recognized and transmitted to the vehicle's OBD system. For the above described converter type, a malfunction of the catalyst exists if and only if the nitrogen oxides present in the exhaust gas are no longer sufficiently reduced over the catalyst for the valid exhaust gas standard. In the case of exceeding the threshold value of the NO2 value fixed by the converter manufacturer, a binary error message is output to the OBD, which in turn can take suitable measures (car repair message on the dashboard display, error message, intervention in the engine control etc.).

In the approach followed here, the catalyst material employed is at the same time used as a selective filter for the $NO_2$ sensor. The second layer of the catalyst serves not only for the catalysis of the reactions $CO+O_2 \rightarrow CO_2$ and $UHC+O_2 \rightarrow CO_2+H_2O$, but also for the catalysis of the reaction $NO+O_2 \rightarrow NO_2$ upon malfunction of the catalyst. Thus, it is achieved that in a normal case only $O_2$ and $CO_2$, which should not cause a sensor signal, will reach the sensors. Upon a malfunction, NO can penetrate into the oxidation layer, where it is reacted to $NO_2$. In addition to the catalysis products $CO_2$ and $O_2$, $NO_2$ also reaches the sensor surface, thus causing an increase of the resistance. The conductivity becomes the lower, the greater the extent of the catalyst's malfunction is. The same applies to the progressing ageing of the catalyst, since the surface with the higher $NO_2$ content grows over the sensor electrode.

Direct Control of the Catalytic Reduction Process

In addition to simple malfunction monitoring, direct control of the converter by the sensor is also conceivable. In the current SCR converters, the reducing agents (e.g., urea) are continuously supplied with the exhaust gas over the catalyst. In the case that the vehicle is not operating, the unreacted urea can freeze in nozzles and other exhaust gas lines. With $NO_x$, HC and ammonia sensors integrated in construction elements, it is possible to introduce the reducing agents into the system only when necessary.

Control and supervision of combustion systems:

Combined with catalytic combustion catalysts, integrated gas sensors can supervise, optimize and record the combustion processes of the air/fuel control introduced through actuators.

System-integrated gas sensors allow for combustion control in mobile systems.

In fuel cells, $H_2$ reformer catalyst and $H_2$ detector:

The function of the Rh-based $H_2$ reformer layers of fuel cells is observed by integrated $H_2$ sensors, and at the same time the concentration and purity of $H_2$ is determined.

The invention claimed is:

1. A device for the qualitative and/or quantitative determination of at least one component of a chemically reducible gas mixture, comprising:
   a) a reduction layer for the chemical reduction of at least one component of the gas mixture;
   b) an oxidation layer for the partial or complete back oxidation of the component(s) chemically reduced by the reduction layer; and
   c) a selective gas sensor electrode for the qualitative and/or quantitative determination of at least one of the back-oxidized components.

2. The device according to claim 1, characterized in that the gas sensor electrode or/and the reduction layer or/and the oxidation layer are bonded to a support substrate.

3. The device according to claim 2, characterized in that the support substrate includes a ceramic honeycomb structure or a metal foil, wherein an electrically non-conductive layer is provided between the metal foil and the gas sensor electrode.

4. The device according to claim 1, characterized in that the component to be reduced/oxidized passes first the reduction layer and then the oxidation layer on its way from the gas mixture to the gas sensor electrode.

5. The device according to claim 1, characterized in that the gas sensor electrode has a thickness within a range of from 1 to 5 µm.

6. The device according to claim 1, characterized in that the gas sensor electrode includes a simple or binary or doped oxide or a semiconductor oxide.

7. The device according to claim 1, characterized in that the reduction and oxidation layers include gas-permeable layers of at least one complex oxide having a spinel, perovskite or aluminate structure and at least one precious metal.

8. The device according to claim 1, characterized in that the reduction layer contains Pd and/or Rh, and/or the oxidation layer contains Pt.

9. The device according to claim 1, characterized in that the reduction layer has a thickness within a range of from 10 to 20 µm, and/or the oxidation layer has a thickness within a range of from 1 to 10 µm.

10. The device according to claim 1, characterized in that at least two gas sensor electrodes are arranged spatially one behind the other with respect to a flow direction of the gas mixture.

11. An exhaust gas catalytic converter or reformer converter, especially a three-way catalytic converter, a selective catalytic reduction (SCR) converter, or an $NO_x$ storage catalytic converter, comprising a device according to claim 1.

12. A vehicle or combustion plant or power generator, comprising an exhaust gas catalytic converter or reformer converter according to claim 11.

13. A process for preparing a device according to claim 1, characterized in that a gas sensor electrode, optionally supported on a support substrate, is provided and coated with oxidation and reduction layers.

14. The process according to claim 13, characterized in that the gas sensor electrode is produced by CVD, PVD, sol-gel, plasma spraying, screen printing, PLD, plating or immersion processes.

15. The process according to claim 13, characterized in that said oxidation and/or reduction layer is prepared by a sol-gel process or an immersion process.

16. A process for monitoring the $NO_x$ emissions of a vehicle according to claim 12, characterized in that the air-to-fuel ratio is varied as a function of the quantity or quantities of the component(s) for which the gas sensor electrode is selective.

17. Use of a device according to claim 1 for the qualitative and/or quantitative determination of at least one component of a chemically reducible gas mixture.

18. The use according to claim 17, characterized in that the component is a pollutant gas, especially an $NO_x$ compound.

19. The use according to claim 17, characterized in that the gas mixture is an exhaust gas of an internal combustion engine.

* * * * *